(12) United States Patent
Johansson et al.

(10) Patent No.: US 8,684,529 B2
(45) Date of Patent: Apr. 1, 2014

(54) SYSTEMS AND METHODS FOR IMPROVED VISUAL FIELD TESTING

(75) Inventors: Göran Anders Johansson, San Francisco, CA (US); Thomas K. Fitzmorris, Palo Alto, CA (US); Vincent Michael Patella, Albany, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 44 days.

(21) Appl. No.: 13/455,722

(22) Filed: Apr. 25, 2012

(65) Prior Publication Data

US 2012/0274905 A1 Nov. 1, 2012

Related U.S. Application Data

(60) Provisional application No. 61/480,300, filed on Apr. 28, 2011.

(51) Int. Cl.
*A61B 3/02* (2006.01)
*A61B 3/00* (2006.01)

(52) U.S. Cl.
USPC .......................... 351/224; 351/237; 351/246

(58) Field of Classification Search
USPC .................................................. 351/200–246
See application file for complete search history.

(56) References Cited

U.S. PATENT DOCUMENTS

| | | |
|---|---|---|
| 3,883,235 A | 5/1975 | Lynn et al. |
| 4,486,080 A | 12/1984 | Itoh et al. |
| 4,669,836 A | 6/1987 | Richardson et al. |
| 4,675,736 A | 6/1987 | Lehmer et al. |
| 4,739,410 A | 4/1988 | Lehmer et al. |
| 4,854,694 A | 8/1989 | Hirano et al. |
| 4,950,069 A | 8/1990 | Hutchinson |
| 5,220,361 A | 6/1993 | Lehmer et al. |
| 5,381,195 A | 1/1995 | Rootzen et al. |
| 5,459,536 A | 10/1995 | Shalon et al. |
| 5,461,435 A | 10/1995 | Rootzen et al. |
| 5,491,757 A | 2/1996 | Lehmer et al. |
| 5,598,235 A | 1/1997 | Heijl et al. |
| 5,807,273 A | 9/1998 | Suzuki |

(Continued)

FOREIGN PATENT DOCUMENTS

| | | |
|---|---|---|
| DE | 4120037 A1 | 12/1992 |
| DE | 4120037 B4 | 9/2004 |

(Continued)

OTHER PUBLICATIONS

International Search Report and Written Opinion received for PCT Patent Application No. PCT/EP2012/057753, mailed on Aug. 16, 2012, 13 pages.

(Continued)

*Primary Examiner* — Mohammed Hasan
(74) *Attorney, Agent, or Firm* — Morrison & Foerster LLP

(57) ABSTRACT

Systems and methods for improving the reliability of visual field test results are presented. In one embodiment, images of the eye are recorded during the presentation of visual stimuli and are displayed to the user to provide information on eye motion, eye position relative to trial lens, and eyelid closure during the test. Individual or combined images can be displayed for individual stimuli, specific test points, or points in the gaze trace in various embodiments of the invention.

25 Claims, 5 Drawing Sheets

(56) References Cited

U.S. PATENT DOCUMENTS

| | | |
|---|---|---|
| 6,527,391 B1 * | 3/2003 | Heijl et al. .................... 351/243 |
| 7,798,643 B2 | 9/2010 | Waldorf et al. |
| 7,942,528 B2 | 5/2011 | Hara |
| 8,132,916 B2 | 3/2012 | Johansson |
| 2004/0057013 A1 * | 3/2004 | Cappo et al. .................. 351/224 |
| 2010/0249532 A1 * | 9/2010 | Maddess et al. ............... 600/300 |

FOREIGN PATENT DOCUMENTS

| | | |
|---|---|---|
| EP | 1602321 A1 | 12/2005 |
| WO | 2009/010291 A1 | 1/2009 |
| WO | 2011/023948 A1 | 3/2011 |

OTHER PUBLICATIONS

Henson et al., "Monitoring Vigilance during Perimetry by Using Pupillography", Investigative Ophthalmology & Visual Science, vol. 51, No. 7, Jul. 2010, pp. 3540-3543.

International Preliminary Report on Patentability received for PCT Patent Application No. PCT/EP2012/057753, mailed on Nov. 7, 2013, 10 pages.

* cited by examiner

SYSTEMS AND METHODS FOR IMPROVED VISUAL FIELD TESTING

PRIORITY

This application claims priority to U.S. Provisional Application Ser. No. 61/480,300, filed Apr. 28, 2011, hereby incorporated by reference.

TECHNICAL FIELD

This invention relates to the field of visual field testing. In particular, the invention discloses systems and methods to improve reliability of visual field test results.

BACKGROUND

Several approaches have been made to monitor and report errors in fixation, eyelid closure, and patient misalignment during visual field measurements in an effort to improve the reliability of visual field testing. Maintaining steady fixation on the central target is vital to accurate mapping of the visual field and for comparing follow-up tests over time. Similarly, complete or partial closure of the eyelids during stimulus presentation also can interfere with visual field measurement. Perhaps less obviously, imprecise translational (x, y and z) and/or rotational placement of the eye relative to the trial lens can also confound visual field test results. It is known to observe the eye under test in a video presentation (see for example U.S. Pat. No. 4,675,736 hereby incorporated by reference). This enables the operator to have a continuous view of the patient's eye position with respect to the trial lens holder to detect obvious deficiencies in the field test. Unfortunately, the operator may be either periodically absent or attending other tasks which divert his attention from the video presentation. Further, the operator cannot determine gaze direction from the video display and typically is unaware of when the actual point is presented, the only time when gaze direction is important.

One approach to gaze direction error detection is the Heijl-Krakau technique, in which a bright stimulus is intentionally projected to an assumed blind-spot of the patient's eye. If the patient's gaze is not on the fixation target, a portion of the retina capable of sight is now in the assumed location of the blind spot, and the patient will respond erroneously to the stimulus, which is recorded as a fixation loss. If the fixation losses exceed a predetermined threshold of the total trial, say 20%, the operator is notified. While useful, this method is problematic in that the anatomic blind spot is not always where predicted, which can lead to erroneous recordings of fixation losses. Additionally Heijl-Krakau monitoring increases overall testing time.

Alternatively, gaze tracking combining video measurement of locations of reflections off the corneal surface with detection of pupil center location have been incorporated into commercial devices. (See for example HFA-II Carl Zeiss Meditec Inc Dublin, Calif. and U.S. Pat. Nos. 5,220,361 and 5,491,757 hereby incorporated by reference). The gaze tracker records patient gaze error during each stimulus presentation, along with pupil position in the lateral dimension relative to the trial lens. Several stimulus presentations must be made at a given perimetric test point in order to determine the minimum brightness that can be seen at that location—the threshold. If the measured sensitivity at a test point location is normal or nearly normal, that result probably did not happen by accident. However, if the sensitivity is lower than normal, that result might have happened because of genuine loss of visual sensitivity, or because—during one or more of the stimulus presentations required to determine threshold sensitivity—the eye was not centered behind the trial lens holder (thus allowing the trial lens holder to block the patient's vision in that part of the visual field), or the head and eye were tilted around the visual axis, allowing the stimulus to be presented at the wrong retinal location, or because the eyelid was partially or completely closed, or because the patient was not looking where s/he was supposed to be looking. Typically, gaze trackers provide a graph of gaze deviation amplitude over time (gaze graph), but do not connect the fixation error with a specific test location in the visual field. Clinical gaze trackers provide only limited quantitative gaze error data and may not quantify other types of issues, e.g., partial eyelid closure or trial lens blocking parts of the field of view. Furthermore, there is no way for the doctor to retrospectively determine the cause of a depressed measurement.

SUMMARY

It is therefore an object of the present invention to provide the doctor with additional information vital to determining the reliability of a visual field test, and also the reliability of the results at its individual test point locations. This is achieved by recording an image of the eye for each stimulus presentation and storing those images for review at any point in time during or after the test. Thus, the doctor can at any time review a suspect defect at a specific test point location and from the stored eye image(s) easily determine if the apparent visual field defect might have been artifactually caused by gaze errors, a closed or droopy eyelid, or blockage by the trial lens frame or excessive tilt of the head. Images could be associated with test locations and with specific measurements on the gaze error plot. This invention will help doctors identify unreliable test results and to have greater confidence in results that do not show such potential causes of artifactual findings.

DETAILED DESCRIPTION

Figure 1:
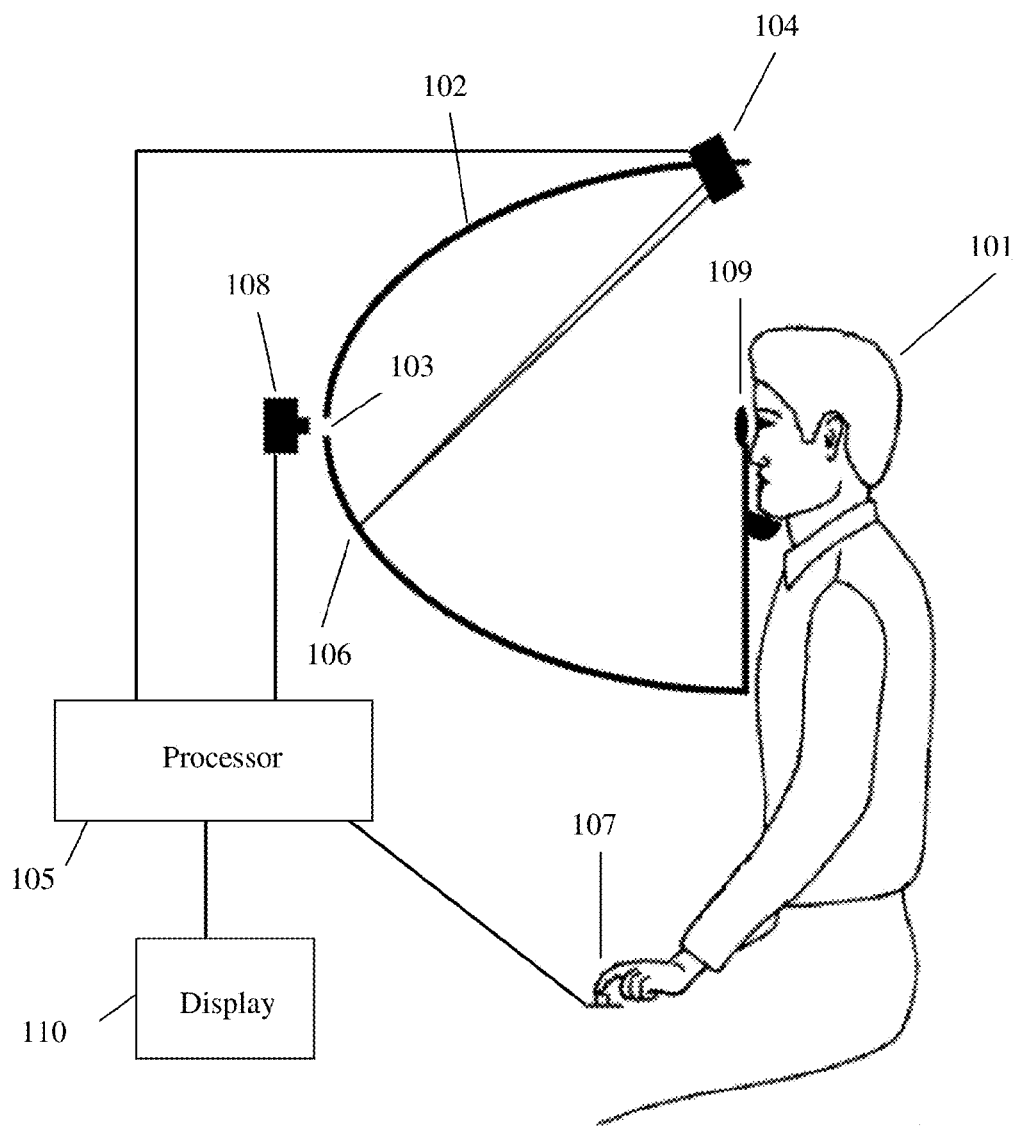
FIG. 1 illustrates one example of a visual field test instrument that can be used to practice the present invention.

The invention described herein could be used in conjunction with any type of visual field tester. One such system is illustrated in FIG. 1. A patient 101 is shown observing a hemispherical projection screen 102. The patient is instructed to fixate at a point at the center of the hemispherical screen 103. A projector 104 under control of a processor 105 projects a series of spots 106 onto the screen. The patient indicates that the spot 106 of light was seen by depressing button 107. The response is recorded by the processor 105. A camera 108 can be used to monitor the gaze of the patient throughout the test. The images from the gaze camera can optionally be displayed (on display 110) to the clinician for aid in patient alignment or test verification. A trial lens holder 109 is positioned in front of the eye of the patient being tested to correct the refractive error of the patient. While FIG. 1 shows a projection type visual field tester, the subject invention can be used with other types of testers, including those that generate images through LCD or other displays. (See for example U.S. Pat. No. 8,132,916 hereby incorporated by reference).

Figure 2:
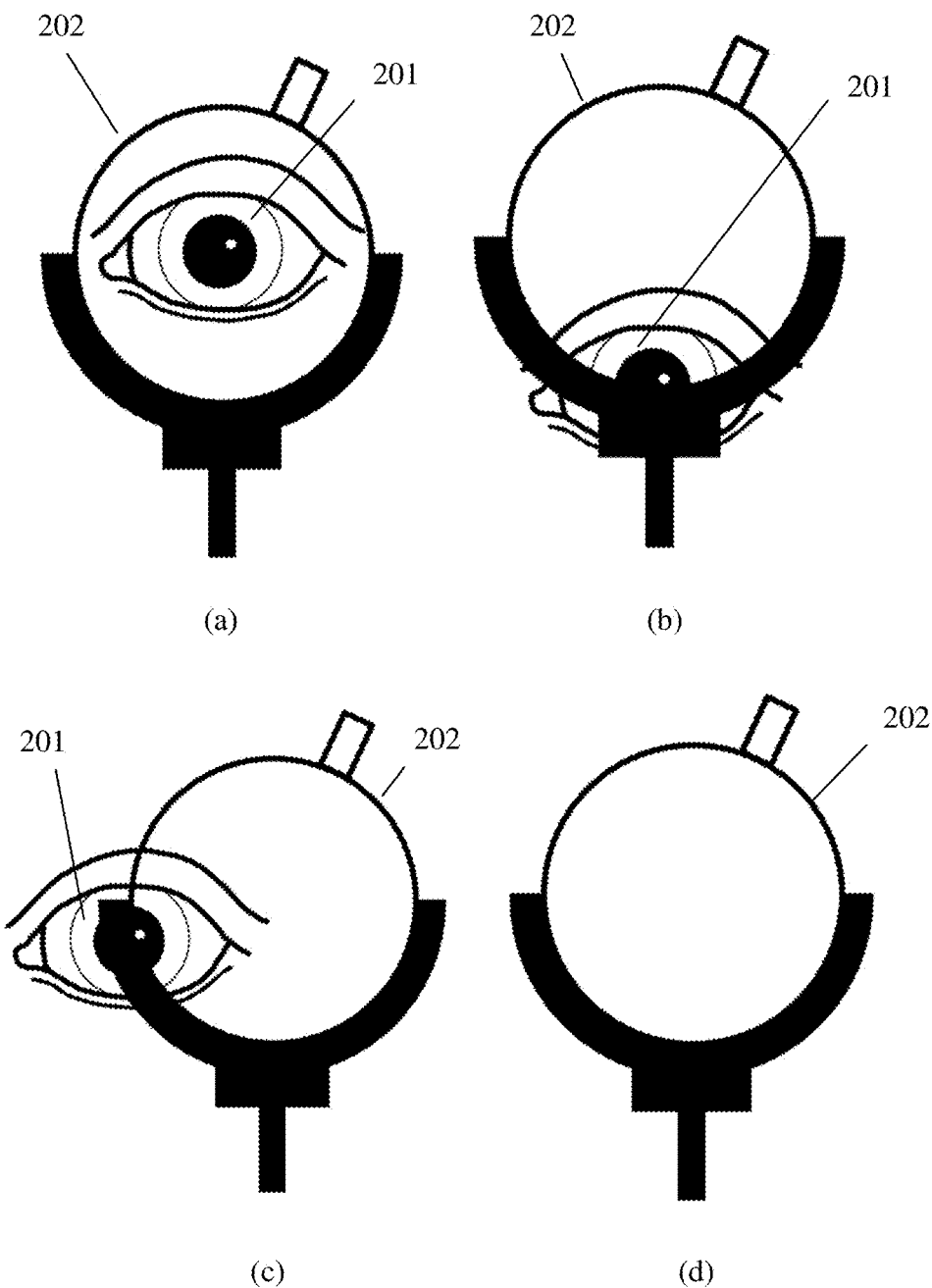
FIG. 2 illustrates the position of the eye relative to the trial lens in the cases of (a) optimum positioning, (b) vertical displacement, (c) horizontal displacement, and (d) total absence of eye.

The invention described herein provides doctors with additional vital information when evaluating a perimetry test having a suspect result. Alone or in addition to gaze, pupil and vertex tracking, the perimeter encompassing the current invention provides an image associated with each stimulus presented during the visual field test. In one embodiment of the present invention, a camera would record images of the eye and a small area around it including the trial lens and trial lens holder. Examples of such images are shown in FIG. 2. FIG. 2(a) shows the eye 201 properly positioned behind the trial lens 202 as would be desired. FIG. 2(b) shows when the eye 201 is low relative to the trial lens 202 and FIG. 2(c) shows when the eye 201 is laterally displaced from the trial lens 202. FIG. 2(d) shows the complete absence of the eye that would result if the patient has temporarily removed their head away from the perimeter. The images are recorded preserving their connection to a specific event in the visual field test (i.e. stimulus presentation) and are available to the doctor or technician for review during the analysis of data from a patient exam. The power that this provides is an objective way for the doctor to evaluate the condition of the patient during a stimulus. If there are outliers of non-response, the doctor now has a way to confirm that the patient's eye was open or closed during that stimulus. This will be a powerful new tool for the clinician and will increase the confidence in the exam information.

The camera taking the images could be the gaze tracker camera or an additional camera. The preferred embodiment uses the same camera to minimize system cost and complexity. The camera records and stores one or more image of the eye during each stimulus presentation. This could lead to the collection of anywhere from tens to hundreds of images per visual field test depending on the testing conditions. Alternatively the gaze tracker camera could record and store a full length movie during the test and provide time stamps when each stimulus is presented. Additionally, images could also be collected between stimulus presentations to provide details on the patient's overall attention throughout the test duration.

Once the images are recorded, various uses for the collected images can be imagined. The stored images taken at the various stimulus presentations can be composed into a short movie that can be played on request or automatically after the test. The movie would provide information to the clinician that a traditional gaze tracker does not provide, e.g., patient's attention during test, sleepiness associated for instance with changes in pupil size, droopy eyelids, trial lens artifacts and eye alignment to the perimetry optics and bowl. Specific frames in the movie could be linked to specific test locations or the gaze graph provided by the gaze tracker.

The total image sequence could be combined into a single image or indicator of the patient's fixation throughout the test, which is displayed on the screen or printed on the test report. This summary image could be created by averaging, summing or other means to provide a summary of the patient's overall attention during the exam. Examples of such summary images are shown in FIGS. 3 and 4.

Figure 3:
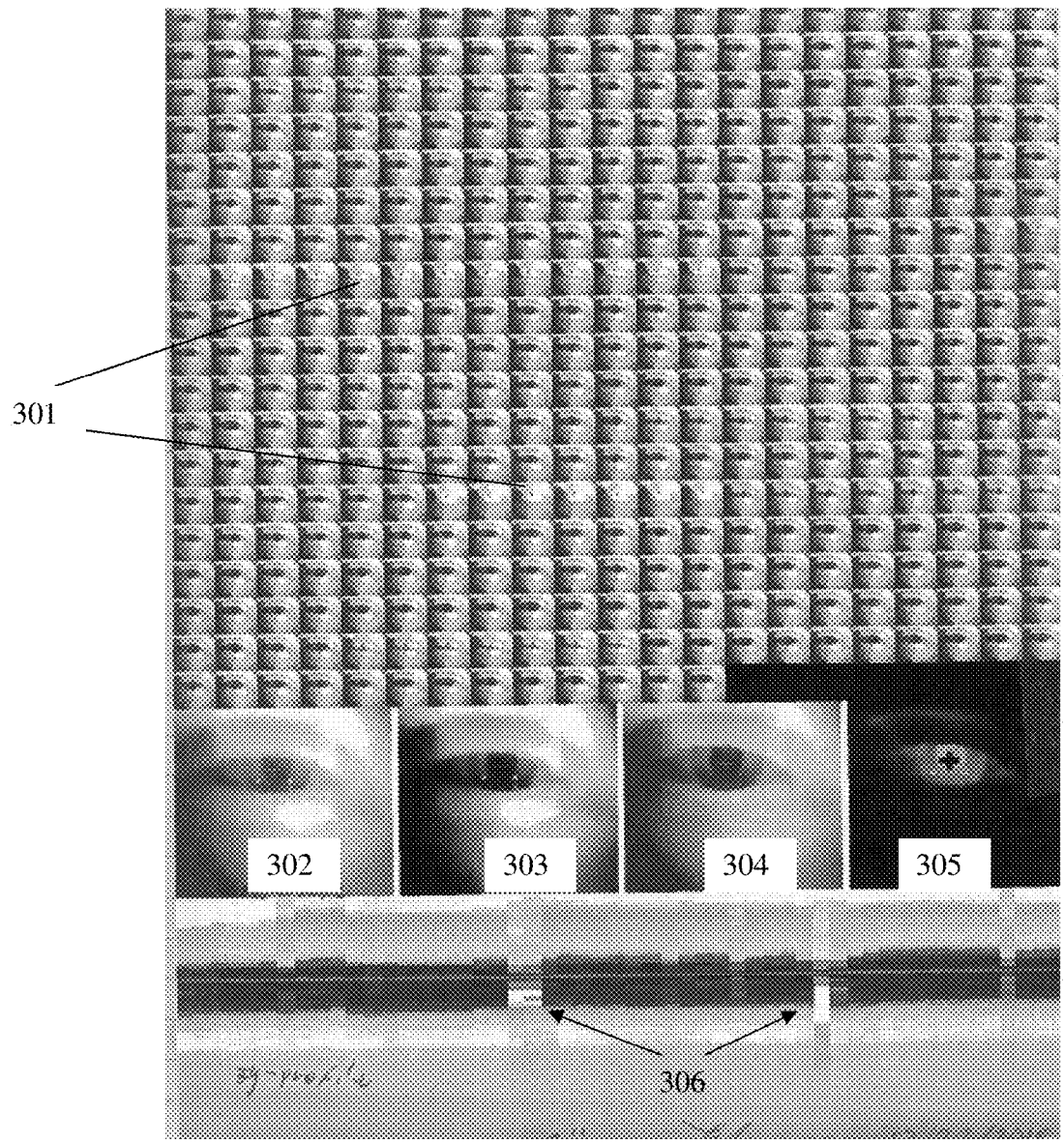
FIG. 3 shows a stream of gaze images (top) and multiple options for analyzing the images to provide information to the instrument operator or clinician (bottom) for the case of good patient fixation.

The top portion of FIG. 3 shows a series of gaze images that were collected of a patient's eye during a visual field exam. While the images are displayed side by side here, the preferred embodiment would be to display one or more images linked to a specific stimulus presentation or alternatively combine some or all the images into a movie format. The images in this figure illustrate a patient with good fixation, as the eye remains centered in the majority of the images. Blinks 301 are evident in several locations in the series. The four large images illustrate possible ways to combine the individual images on a pixel by pixel basis into a summary image, by calculating the average value of the pixels from multiple images 302, calculating the total sum of the data for corresponding pixels in each image 303, taking the minimum intensity value at a particular pixel in a collection of images 304, or by calculating the standard deviation of the different intensity values for a collection of images 305. The bottom most portion of the figures shows an alternative way to combine the series of images, by combining a single vertical slice of data from the central portion of each image in the order they were recorded so that the lateral axis in this plot represents time. The locations denoted by arrow 306 highlight images recorded during patient movement or blinks.

Figure 4:
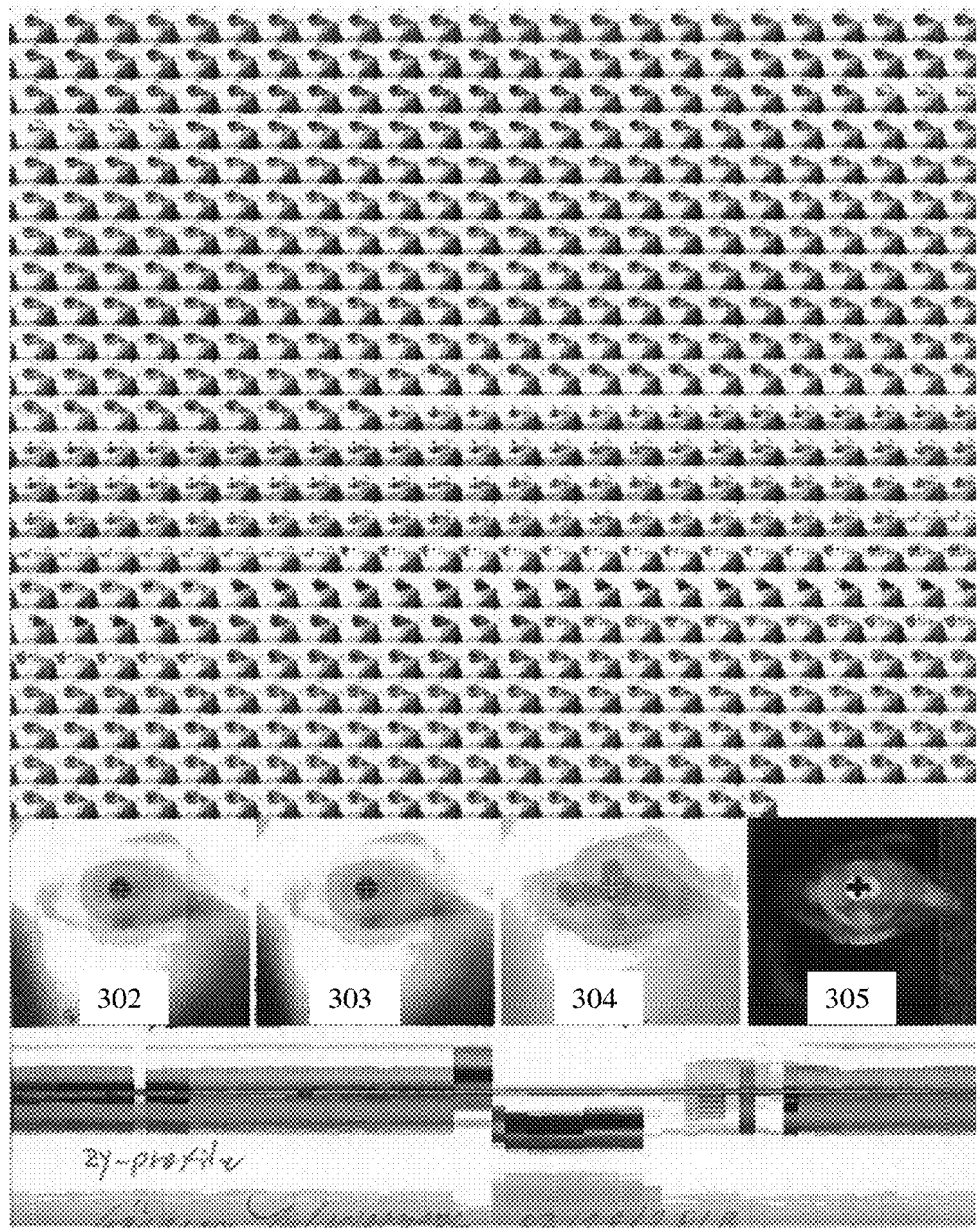
FIG. 4 shows a stream of gaze images (top) and multiple options for analyzing the images to provide information to the instrument operator or clinician (bottom) for the case of bad patient fixation

FIG. 4 contains the same information as FIG. 3 but in the case of a patient with bad fixation. Similar to FIG. 3, the top portion shows a series of individual images while the four large images illustrate possible ways to combine all individual images into a summary image, by calculation of the average 302, the sum 303, the minimum 304, or the standard deviation 305. The blurring evident in the summary images is indicative of changes in the patient's gaze over the test duration and might be used qualitatively or reduced to a figure or figures of merit and compared to normative data. A quantitative indicator of the blur could be determined and displayed to the clinician as an indicator of reliability.

The images may be sorted according to stimulus location, for example, 1-20 images per test point location and displayed based on input from the clinician. For each test point location, the eye images may be individually displayed, or played as a movie or provided as a summary image (averaged, summed or other means).

Figure 5:
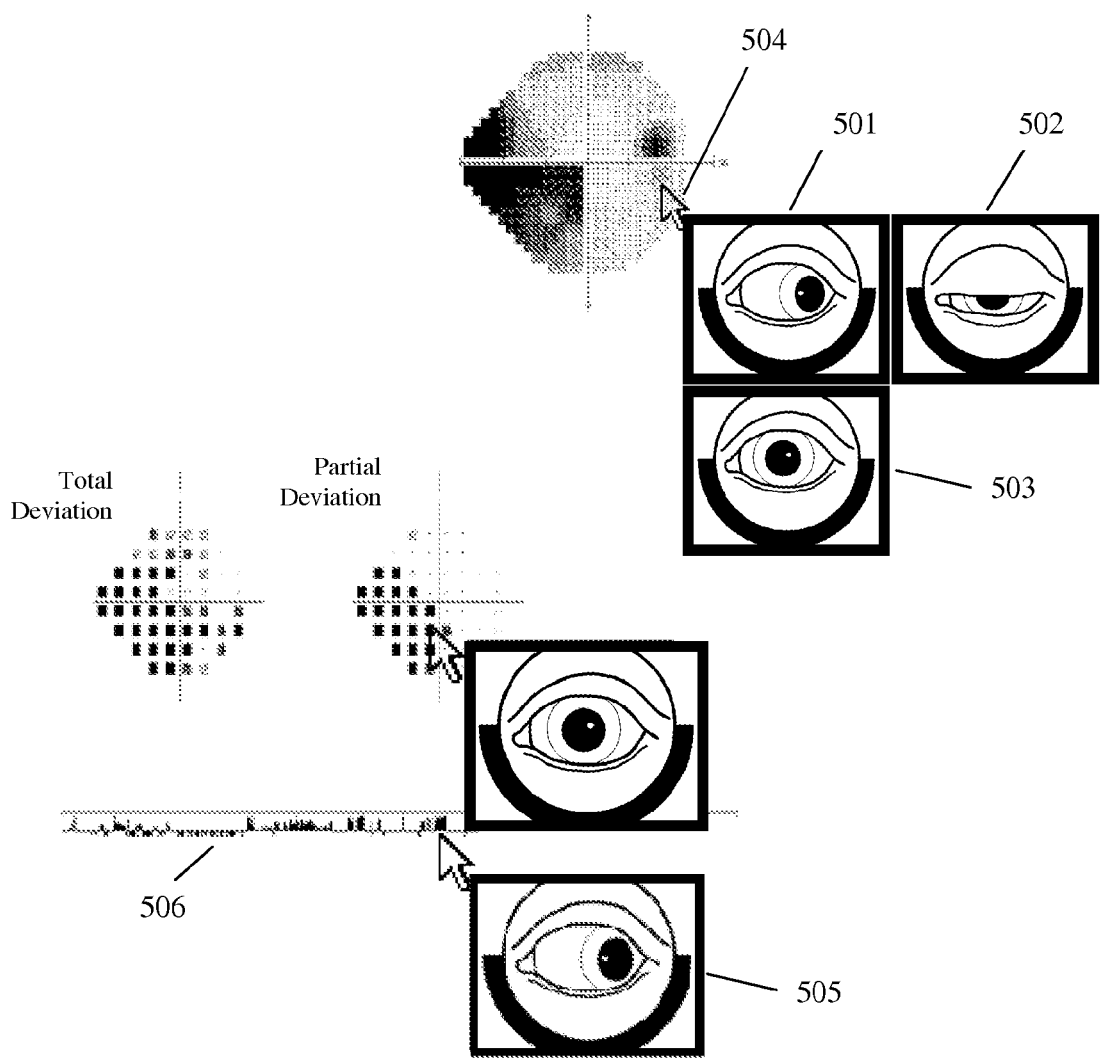
FIG. 5 illustrates how gaze images could be used to enhance the information available to the clinician when reviewing visual field test results.

The doctor or technician can click-on, touch, roll-over, or in some other way select a defect shown on the visual field test result, or any test point on any processed, derived or analyzed test result (greytone, PD, TD, etc), and have the gaze tracking points corresponding to that location "light up" i.e. be highlighted and have the eyeball image or images taken during each stimulus presented at that location be displayed above those gaze tracking lines. For example four images could pop-up just above the gaze tracker graphs and the adjacent test report on the screen could simultaneously highlight the same test point that the user is touching or pointing to, as well as the respective gaze track lines and corresponding photos from that study. FIG. 5 shows one embodiment of such a display. A popup window with one or more images of the eye can be provided automatically to examine suspected test locations. Inspection of the eye images will tell "at a glance" whether the patient's eye was centered in the trial lens, identify lid artifacts, whether the lid was closed (patient dozing off) or whether the patient's gaze was obviously off to the side (poor fixation). This helps the doctor to determine the likelihood that a visual field defect is valid or invalid. Images 501, 502 and 503 were collected during individual stimuli presentation used to determine an individual test point indicated by arrow 504. Image 501 indicates a change in gaze direction and image 502 indicates a droopy eyelid both of which would discredit the reliability of the data at that test point. The specific points in the gaze tracker's gaze deviation amplitude trace associated with a measured threshold might be highlighted—and even color coded to the gaze image(s). Image 505 is linked to a particular point in the gaze trace 506. The gaze tracker could provide a numerical value of the gaze error for that specific eye image or the images might be color coded according to the amount of gaze error measured.

While most embodiments of the invention are qualitative in nature, the invention described herein is likely to be enormously useful as a fast quality control step, especially if a defect appears that is suspicious, say because on the prior test there was no defect, or vice versa: the prior test has a test point with a defect that now is gone. This would lead to a further implementation: show the current and prior study report side by side on-screen and the user can roll over or touch any test point and the respective test point and relevant gaze track and eyeball images for both exams would be displayed simultaneously.

The technician or doctor can label (color, symbol, etc.) and store test locations where non-valid visual field defects are present for future reference. Labeling can be made with a single label or labels identifying the type of error, e.g., gaze error, eyelid defect or trial lens defect.

The technician or doctor might use test results from two or more tests to construct a composite test in which the results judged to be most reliable are used, averaged, or otherwise combined. This would allow clinicians to salvage test results and to improve the reliability of data used in diagnosis and follow-up. A baseline consisting of a composite test might be more reliable and representative of the patient's true medical status at the beginning of treatment than any single test. Similarly, follow-up tests, e.g. at a crucial juncture in the patient's management, might be combined into a composite test that is more representative of the patient's medical status than any single test. The composite test could be based on only results deemed reliable based on the collected images. It could also be based on feedback from the gaze tracker. These calculations might be applied, for instance to the two tests chosen to comprise a patient's baseline, producing a composite baseline that more is accurately representative of the patient's true visual field status—as compared to simply averaging the two results. This could be achieved at the level of disregarding individual threshold measurements, or at the level of disregarding specific patient responses. In the latter case, the field would be recalculated from an aggregate response list file, e.g. using visual field models such as the one already extant in the Swedish Interactive threshold algorithm (SITA, see for example U.S. Pat. Nos. 5,461,435, 5,381,195, and 5,598,235)

The response list files of multiple test results in which specific responses have been eliminated might be combined using a visual field model such as that present in the SITA algorithms of the HFA. The combined response list files could then be used to objectively produce a composite test as described above.

Identified and labeled non-valid test locations or even single questions can be optionally excluded from further analysis, e.g., in Guided Progression Analysis (GPA), Visual Field Index (VFI), and progression analysis. Exclusion of labeled single responses might also be used to modify the inputs used by the thresholding algorithm to determine visual sensitivity. Elimination of clearly invalid data may improve the reliability of the analysis.

The gaze tracker currently stores information regarding the location of the pupil center and first Purkinje reflex (the reflection from the outer surface of the cornea). The gaze tracker associates these coordinates with each stimulus presentation. It could therefore be advantageous to indicate the location of these points in the presentation of the eye images as described above. This would give additional information on reliability of the gaze tracker. For example, it should be relatively easy to see that the gaze tracker detected a reflex in the tear film near the eyelid instead of the correct location of the first Purkinje reflex.

While the description above focuses on post-processing and review of visual field test data, features can be made available to the perimetrist during the test and would allow for errors to be detected on the fly. The clinician or perimetrist might optionally request the instrument to retest locations with errors, or simply re-instruct the patient and restart or resume the test.

Although various embodiments that incorporate the teachings of the present invention have been shown and described in detail herein, those skilled in the art can readily devise many other varied embodiments that still incorporate these teachings.

The following references are hereby incorporated by reference

U.S. Pat. No. 4,675,736 Lehmer et al. "Superimposed analog video image on plotted digital field tester display"

U.S. Pat. No. 5,220,361 Lehmer et al. "Gaze tracking for field analyzer"

U.S. Pat. No. 5,381,195 Rootzen et al. "Method and apparatus for testing a subject's perception of visual stimuli"

U.S. Pat. No. 5,459,536 Shalon et al. "Apparatus and Method for Automated Perimetry"

U.S. Pat. No. 5,461,435 Rootzen et al. "Method and an apparatus for checking the thresholds of a subject's perception of visual stimuli"

U.S. Pat. No. 5,491,757 Lehmer et al. "Field tester gaze tracking using content addressable memories to improve image data analysis speed"

U.S. Pat. No. 5,598,235 Heijl et al. "Method and an apparatus for testing a subject's response to visual stimuli"

U.S. Pat. No. 5,807,273 Suzuki et al. "Ophthalmic Apparatus"

U.S. Pat. No. 7,942,528 Hara et al. "Perimeter"

U.S. Pat. No. 8,132,916 Johansson et al. "High precision contrast ratio display for visual stimulus"

WO 2011/023948 Pelah et al "Visual Perimeter Measurement System and Method"

What is claimed is:

1. A method for providing information on the reliability of a visual field test given to a patient, said method comprising:
    sequentially presenting visual stimuli to the patient at different locations in space during the field test;
    capturing a series of images of the eye throughout the visual field test, said images being temporally associated with the presentation of a particular stimuli during the test;
    storing the images wherein the storing preserves the temporal association between the image and the presentation of the particular stimuli for later recall;
    displaying a map of test points corresponding to the results of the field test; and
    in response to the selection of a particular test point from within the map, displaying one or more of the images of the eye captured when the associated stimuli was presented.

2. A method as recited in claim 1, wherein the one or more images are associated with measured gaze errors provided by a separate gaze tracker.

3. A method as recited in claim 2, further comprising visually indicating the points in a gaze deviation amplitude trace associated with the one or more images.

4. A method as recited in claim 3, wherein images are linked to particular points in the gaze deviation amplitude trace.

5. A method as recited in claim 1, wherein the one or more images are displayed in the form of a movie.

6. A method as recited in claim 1, wherein the display of the one or more images is selectable by an operator based on a suspect result of the visual field test.

7. A method as recited in claim 1, further comprising processing one or more images into a single image.

8. A method as recited in claim 7, wherein the processing involves one of averaging, summing, determining the minimum, or calculating the standard deviation at each pixel for the collection of images.

9. A method as recited in claim 7, wherein the single image is generated by combining single vertical slices of date from the central portions of the one or more images in the order they were recorded.

10. A method as recited in claim 7, further comprising determining a quantitative indicator from the processed image.

11. A method as recited in claim 1, further comprising disregarding specific test point results or individual stimuli based on the images.

12. A method as recited 11, wherein the test point results or stimuli are disregarded manually.

13. A method as recited in claim 11, wherein the test point results or stimuli are disregarded automatically.

14. A method as recited in claim 11, wherein the test point results or stimuli are disregarded based on information from a gaze tracker.

15. A method as recited in claim 1, further comprising comparing the one or more images to one or more images collected from a previous exam associated with the same event.

16. A method for providing information on the reliability of a visual field test, said method comprising:
    capturing a series of images of the eye throughout the visual field test, said images being temporally associated with known events in the test;
    storing the images wherein the storing preserves the temporal association between the image and the known event for later recall;
    processing one or more images into a single image;
    wherein the processing involves one of averaging, summing, determining the minimum, or calculating the standard deviation of the collection of images; and
    displaying the processed image.

17. A method as recited in claim 16, further comprising determining a quantitative indicator from the processed image.

18. A method for providing information on the reliability of a visual field test, said method comprising:
    capturing a series of images of the eye throughout the visual field test, said images being temporally associated with known events in the test;
    storing the images wherein the storing preserves the temporal association between the image and the known event for later recall; and
    disregarding specific test point results or individual stimuli based on the images:
    constructing a composite test based upon threshold sensitivity results from multiple tests, using only results or stimuli that have not been disregarded;
    displaying information related to the composite test.

19. A visual field testing apparatus for evaluating the field of vision of a patient and providing information regarding artifacts arising during measurement, said artifacts being caused by factors such as eye movement and eyelid closure, said apparatus comprising:
    an interface for displaying visual stimuli at different locations on the interface at different times during the field test;
    a camera for capturing images of the eye of the patient during the field test;
    a display for displaying images of the eye derived from image information captured by the camera; and
    a processor for controlling the interface and receiving images from the camera and associating image information with particular visual stimuli, said processor generating a map of test points corresponding to the results of the field test and, in response to the selection of a particular test point from within the map, causing one or more of the images of the eye captured when the associated stimuli was presented to be displayed on the display.

20. An apparatus as recited in claim 19, wherein said processor generates a composite image comprising a plurality of images of the eye captured during the field test, the composite image indicating the extent of measurement error caused by artifacts.

21. A method of evaluating the visual field of a patient, providing information regarding artifacts arising during measurement, said artifacts being caused by factors such as eye movement and eyelid closure comprising the steps of:
    selectively presenting visual stimuli to the patient at different locations in space during the field test;
    recording the response of the patient to the stimuli;
    capturing images of the eye as the visual stimuli are being presented;
    generating a map of test points corresponding to the results of the field test; and
    in response to the selection of a particular test point from within the map, displaying an image or images of the eye captured at times when the visual stimuli associated with the selected test point was presented to the patient.

22. A method as recited in claim 21, wherein the one or more images are associated with measured gaze errors provided by a separate gaze tracker.

23. A method as recited in claim 21, further comprising processing one or more images into a single image.

24. A method as recited in claim 21, further comprising disregarding specific test point results or individual stimuli based on the images.

25. A method as recited in claim 21, further comprising comparing the one or more images to one or more images collected from a previous exam associated with the same event.

* * * * *

UNITED STATES PATENT AND TRADEMARK OFFICE
CERTIFICATE OF CORRECTION

| | |
|---|---|
| PATENT NO. | : 8,684,529 B2 |
| APPLICATION NO. | : 13/455722 |
| DATED | : April 1, 2014 |
| INVENTOR(S) | : Göran Anders Johansson et al. |

It is certified that error appears in the above-identified patent and that said Letters Patent is hereby corrected as shown below:

In the Specification

In column 2, line 54, Delete "fixation" and insert -- fixation. --, therefor.

In column 5, line 51, Delete "5,598,235)" and insert -- 5,598,235). --, therefor.

Signed and Sealed this
Twenty-fourth Day of June, 2014

Michelle K. Lee
*Deputy Director of the United States Patent and Trademark Office*